United States Patent [19]

Blum

[11] Patent Number: 4,663,516
[45] Date of Patent: May 5, 1987

[54] HEATING BED

[76] Inventor: Manfred Blum, Dierdorfer Str. 4, 5451 Rüscheid, Fed. Rep. of Germany

[21] Appl. No.: 763,148
[22] PCT Filed: Nov. 22, 1984
[86] PCT No.: PCT/DE84/00249
  § 371 Date: Jul. 23, 1985
  § 102(e) Date: Jul. 23, 1985
[87] PCT Pub. No.: WO85/02331
  PCT Pub. Date: Jun. 6, 1985

[30] Foreign Application Priority Data

Nov. 23, 1983 [DE] Fed. Rep. of Germany ....... 3342180

[51] Int. Cl.⁴ .................. H05B 3/20; A47C 21/04; A61F 7/00
[52] U.S. Cl. ................................ 219/217; 5/449; 5/424; 5/421; 219/201; 219/378; 219/521
[58] Field of Search .................. 128/376; 5/448, 449, 5/424, 421; 126/205, 400; 219/217, 200, 201, 439, 521, 462, 378

[56] References Cited

U.S. PATENT DOCUMENTS

| 3,322,113 | 5/1967 | Simjian | 219/439 |
| 3,428,973 | 2/1969 | Hargest | 5/449 |
| 3,585,356 | 6/1971 | Hall | 219/217 |
| 3,924,284 | 12/1975 | Nelson | 219/217 |
| 4,498,205 | 2/1985 | Hino | 5/449 |

Primary Examiner—George H. Miller, Jr.
Assistant Examiner—Teresa J. Walberg
Attorney, Agent, or Firm—Becker & Becker, Inc.

[57] ABSTRACT

A heating bed for therapeutic heat treatment. The heating bed includes a container for accommodating a sand filling which may be heated to a predetermined temperature via a heating device. The sand filling is covered by a cover which is preferably made of textile material.

7 Claims, 3 Drawing Figures

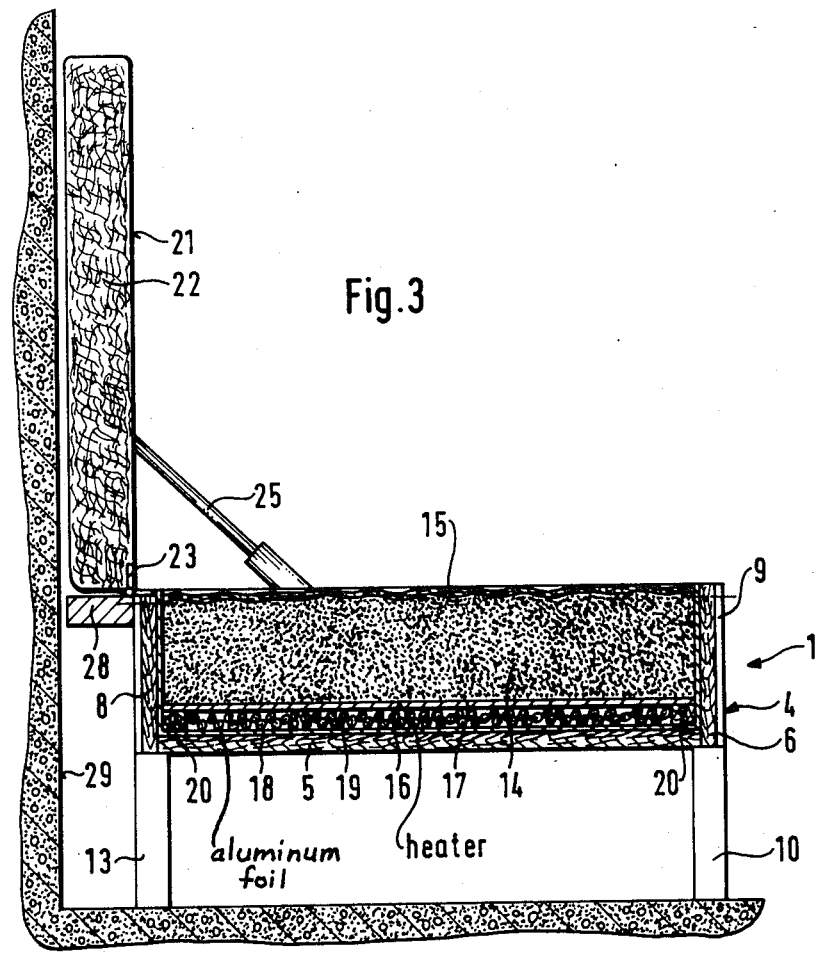

4,663,516

HEATING BED

BACKGROUND OF THE INVENTION

The present invention relates to a heating bed, which is especially intended for therapeutic purposes.

1. Field of the Invention

It is known that the use of heat can considerably relieve the pain caused by rheumatic pains, wear and tear of the skeleton, especially of the spine, and the pains resulting therefrom, and similar bodily ailments. For the most part, the heat treatment in such cases is carried out outside the home of the person afflicted in special institutions, such as hospitals or the treatment rooms of doctors. The drawback to this is that on the one hand such a treatment can only very unsatisfactorily follow the individual requirements of an adapted treatment program; furthermore, the success of the treatment can be more or less called in question due to the fact that after the treatment the afflicted person must on his way home, for example in an unheated vehicle, be exposed to unfavorable climatic conditions for a more or less long period of time, especially with regard to low outside temperatures.

2. Description of the Prior Art

The invention therefore proceeds from the idea that the success of heat treatment can on the average be considerably improved if the treatment is carried out in the home of the afflicted person. Accordingly, it is an object of the present invention to provide an apparatus which, with regard to the aforementioned field of bodily illnesses, makes it possible in particular to carry out heat treatment in the home of the afflicted person. Such an apparatus can, of course, also be used in clinics and similar treatment centers.

SUMMARY OF THE INVENTION

To resolve this object, the present invention proposes a heating bed or bed-like heating apparatus which is characterized by a box-like container which is opened toward the top for receiving fine-grained, heat-storing material, especially sand, and is furthermore characterized by a heating device, for the aforementioned material, located in the container and essentially extending over the entire container, and finally by a textile cover which closes off the top of the container, rests upon the aforementioned material, and is secured to the container. The sand which is utilized is preferably quartz sand or ocean sand.

The inventive apparatus enables an intensive yet very uniform heat treatment of a person resting thereupon, with the sand, preferably quartz sand, causing the heat to be uniformly supplied to all body zones which face the sand. The textile cover, which is preferably placed upon the sand with a certain amount of slack, prevents direct contact of the person resting thereon with this heat-storing and heat-transmitting material. In addition to physiological and hygenic reasons, this textile cover therefore also serves to keep the pertaining room clean.

The heating device is, of course, embodied in such a way that the temperature of the sand, which stores heat and gives it off uniformly to the person resting thereon, can be adjusted, i.e. the temperature can be expediently regulated.

In order to avoid unnecessary loss of heat, it is proposed pursuant to one inventive embodiment to provide a layer of predetermined thickness between the bottom of the container and the aforementioned material, with the layer comprising an insulating material, such as granular, foamed polystyrene.

Furthermore, also with regard to keeping heat loss as low as possible, it is expedient if pursuant to another inventive embodiment there is provided between the bottom and the aforementioned material (e.g. sand) a layer is provided which reflects thermal radiation, for example an aluminum foil possibly coated with a film of plastic.

The heating device can have various forms; various energy carriers can also be used, such as hot air which is circulated through a coil of pipe which is guided in a meander fashion in the sand bed. In a preferred embodiment of the invention, it is proposed that the heating device be embodied as an electrical surface heating element, and that an electrical grounding grid be disposed in the aforementioned material approximately parallel to the plane of the surface heating element. The use of a grounding grid is, of course, obvious.

In order to preclude damage of the electrical surface heating element by the grounding grid, it is possible pursuant to a further inventive embodiment to provide a sheet-like insulating body between the surface heating element and the grounding grid.

In a preferred further embodiment of the present invention, the inventive bed is supplemented by providing the container, which is preferably made of wood and/or wood material, with a cover which can be raised. In so doing, if desired on the one hand the container which serves for the heat treatment can be closed off toward the outside, and on the other hand there hereby results a further utilization possibility for the inventive bed. In conformity with this additional utilization possibility, the cover is expediently padded. Pursuant to another inventive embodiment, the bed may be provided with corner legs which are part of the box-like container. This leads not only to a construction of the inventive bed which is esthetically pleasing, but also to a stable construction which can be economically manufactured.

BRIEF DESCRIPTION OF THE DRAWINGS

The invention is subsequently described in connection with one specific embodiment and with the aid of FIGS. 1 to 3 of the drawing.

Shown is

DESCRIPTION OF PREFERRED EMBODIMENTS

Figure 1:
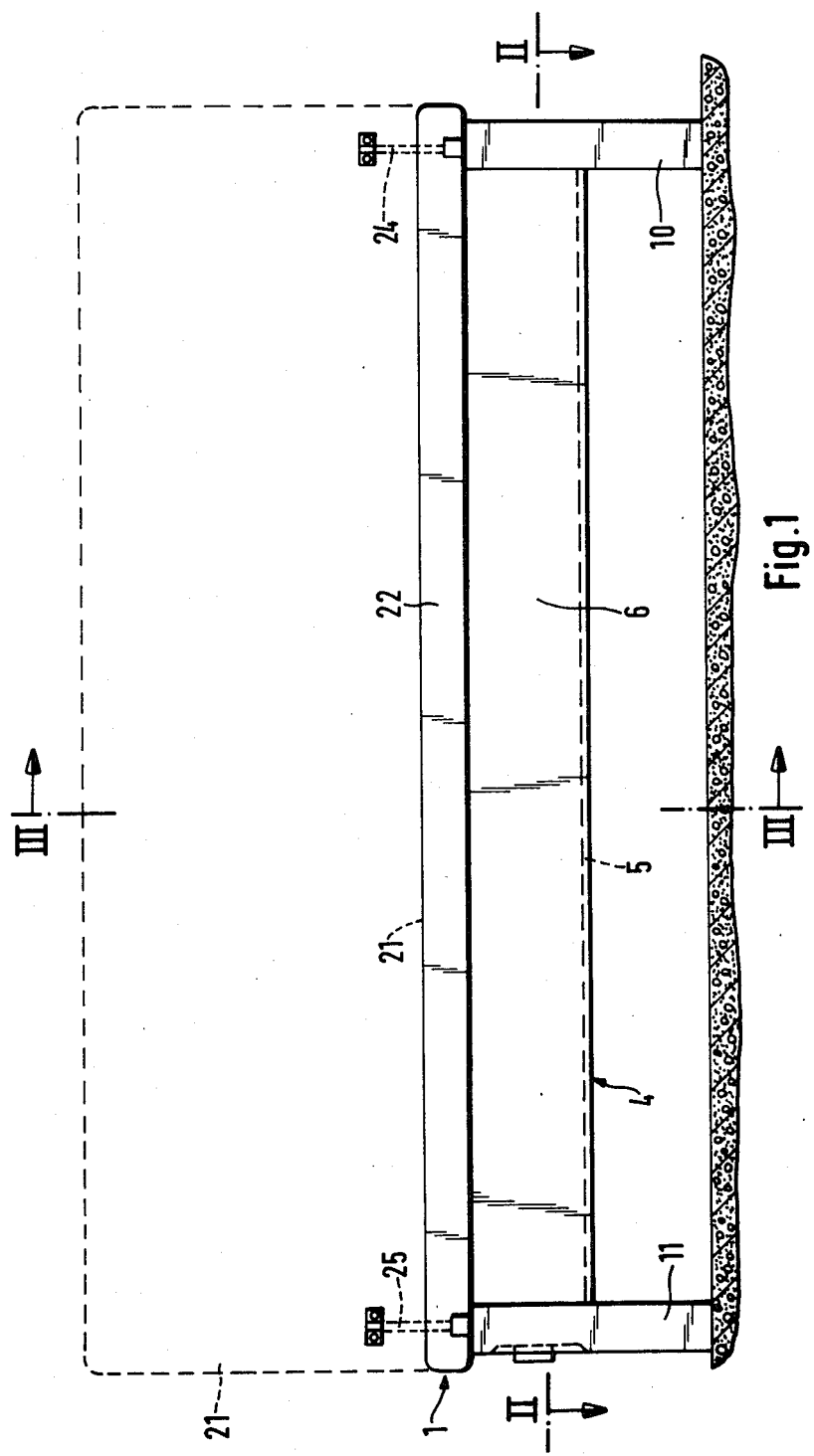
FIG. 1 a front view of the inventive bed.
Figure 2:
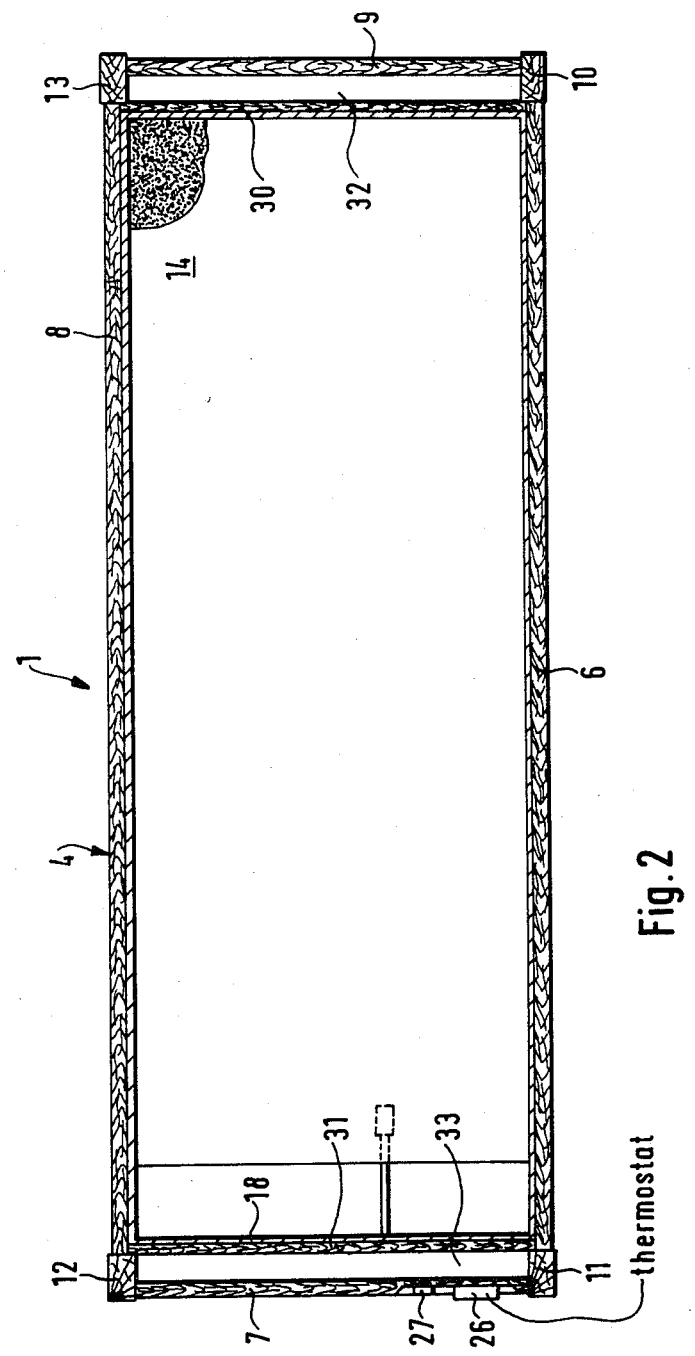
FIG. 2 a sectional view of the bed of FIG. 1 taken along the sectional line 2—2 in FIG. 1, FIG. 3 a side sectional view of the bed of FIG. 1 taken along the sectional line 3—3 in FIG. 1.

The drawings illustrate a bed or couch 1, which essentially comprises a box or container 4 for a sand filling 14 of quartz sand. The container 4 has a bottom 5 which is made, for example, of chip board; together with the side walls 6, 7, 8, and 9, which are preferably made of wood, as well as the corner legs 10, 11, 12, and 13, the bottom 5 forms the container 4. The side walls 6 to 9 and the corner legs 10 to 13 are rigidly interconnected by means of glue and long wooden pegs. The bottom 5, and additional reinforcing strips which are designated with the reference numeral 20, are connected to one another and with the side walls 6 to 9 by means of glue and additionally suitable clamps.

Provided in the vicinity of the bottom 5 of the container 4 is a preferably electrically operated heating device 16 which is embodied as a type of known electrical surface heating unit. Such surface heating units can be coated, for example with electrically conductive material such as pulverized coal, with the remainder being insulated coils. The heating units could, for example, also be wires of electrically conductive material which are disposed in a meandering fashion and are expediently secured in a support netting. Above the heating device 16, which is located in the lower region of the sand filling 14, a grounding grid 17 is provided when the heating device is constructed as an electrical unit in order in each case, and especially in the event of a failure of the heating device, to keep the sand filling 14 free of electrical voltage. The heating device 16 is provided with a non-illustrated regulator which is suitable for keeping the sand filling 14 at a preselectable temperature.

In order to avoid unnecessary loss of heat, there is provided below the heating device 16, and above a polystyrene filling 19 which serves for further insulation, for a filling of similar insulating material, in the sand bed 14, an aluminum foil 18 which reflects thermal radiation and is expediently coated with synthetic material. The aluminum foil 18 expediently extends upward along the side walls 6 to 9 at least to the upper edge of the sand filling 14, where it is secured to the side walls by strips or the like which are not disclosed in detail.

Also secured to the side walls 6 to 9 is a cover 15 which preferably comprises a textile material of sufficient thickness; the cover 15 is preferably disposed on the sand filling 14 with a certain amount of slack. Thus, a person who is lying on the sand filling 14, with this cover 15 being interposed between the person and the sand filling, does not come into direct contact with the latter; furthermore, the aforementioned slack of the cover 15 even permits as great an adaptation as possible of the heat-transmitting sand to the contours of the body of the person lying thereon.

As a closure means, and with regard to an additional utilization possibility of the inventive bed—especially after heat treatment has been completed—a cover 21 is disposed on the container 4 by means of hinges 23 or similar joints. The cover 21 is provided with padding 22, so that an unlimited utilization possibility exists for the inventive bed to function merely as a rest.

In order to keep the cover 21 in an appropriate open position when the bed is being used for heat treatment, supports 24 and 25 are expediently provided; these supports, which are expediently embodied as known gas springs, are pivotably connected on the one hand on parts, especially the side walls, of the container 4, and on the other hand on the cover.

In order to receive the supports 24 and 25, one end of which is pivotably connected with the side walls 7 or 9, and the other end of which is pivotably connected with the cover 21, grooves 32 and 33 are provided within cross bars 30 and 31 respectively which are associated with the container 4 via a respective one of the pertaining side walls 7 and 9. The cross bars 30 and 31 extend to the bottom 5 of the container 4, with glue being used, for example, to connect the ends with the pertaining side walls 6 and 8, and the longitudinal sides with the bottom 5. The grooves 32 and 33, which serve for receiving the supports 24 and 25, thus prevent dirt from entering and also prevent a possible obstruction in the functioning of the supports 24 and 25, which are preferably embodied as gas springs.

The drawings also schematically illustrate an electrical thermostat 26 and an electrical connection 27, which in this embodiment are disposed on the side wall 7. The sensor of the thermostat 26, which is not shown in detail, extends through the cross bar 31 sufficiently far into the sand filling 14. Instead of attaching the thermostat 26 and the electrical connection 27, and possibly other electrical means, onto or in the side wall 7, it may also be expedient to combine these electrical devices and means in an instrument box which is then placed as a unit into an appropriately sized recess, for example of the side wall 7.

The inventive bed can be advantageously further supplemented by providing a bracket 28 in the region of that longitudinal side of the bed 1 which is provided with the hinge 23; this bracket 28 can be secured, for example on the side wall 8, in a suitable manner. The bracket 28 is expediently of such a width that it is possible to completely raise the cover 21 and arrest it in this position without the cover 21 or the padding 22 thereby coming into contact with the surface of a wall 29 against which that longitudinal side of the bed which carries the bracket 28 is placed.

In addition to the embodiment of the inventive bed illustrated in the drawing and described above, further embodiments are, of course, also conceivable, especially with regard to a somewhat modified construction of the sand bed, without thereby deviating from the scope of protection set out in the claims, and without therefore requiring further particular inventive efforts.

What I claim is:

1. A heating bed, comprising:
   a box-like container which is open toward the top, and which contains a fine-grained, heat-storing material;
   a heating device for said heat-storing material, with said heating device being disposed in said, and essentially extending over the entire, container;
   a flexible cover which is secured to said container, closes off the open top of said container, and rests upon said heat-storing material;
   said container having a bottom; and
   a layer disposed between said bottom and said heat-storing material; said layer having a predetermined thickness, and being made of insulating material, said insulating material of said layer being granular, foamed polystyrene.

2. A heating bed, comprising:
   a box-like container which is open toward the top, and which contains a fine-grained, heat-storing material;
   a heating device for said heat-storing material, with said heating device being disposed in said, and essentially extending over the entire, container;
   a flexible cover which is secured to said container, closes off the open top of said container, and rests upon said heat-storing material;
   said container having a bottom; and
   a layer disposed between said bottom and said heat-storing material, said layer reflecting thermal radiation.

3. A heating bed according to claim 2, in which said reflecting layer is an aluminum foil which is coated with synthetic material.

4. A heating bed, comprising:

a box-like container which is open toward the top, and which contains a fine-grained, heat-storing material;

a heating device for said heat-storing material, with said heating device being disposed in said, and essentially extending over the entire, container;

a flexible cover which is secured to said container, closes off the open top of said container, and rests upon said heat-storing material;

said heating device being in the form of an electrical surface heating element; and an electrical grounding grid which is disposed in said heat-storing material approximately parallel to the plane of said surface heating element.

5. A heating bed according to claim 4, which includes a sheet-like insulating body disposed between said surface heating element and said grounding grid.

6. A heating bed, comprising:

a box-like container which is open toward the top, and which contains a fine-grained, heat-storing material;

a heating device for said heat-storing material, with said heating device being disposed in said, and essentially extending over the entire, container; and a flexible cover which is secured to said container, closes off the open top of said container, and rests upon said heat-storing material;

said container being provided with a further cover, which can be raised;

grooves includes in the region of said container; and supports which are accommodated in said grooves, and are connected to and movable with said further cover.

7. A heating bed according to claim 6, which includes a housing in which are combined electrical devices and means for the operation of said heating device, with said housing also being accommodated by said grooves.

* * * * *